United States Patent
Mikami

(10) Patent No.: US 10,620,124 B2
(45) Date of Patent: Apr. 14, 2020

(54) OPTICAL ANALYSIS DEVICE AND BIOMOLECULAR ANALYSIS DEVICE

(71) Applicant: HITACHI, LTD., Chiyoda-ku, Tokyo (JP)

(72) Inventor: Hideharu Mikami, Tokyo (JP)

(73) Assignee: HITACHI, LTD., Tokyo (JP)

( * ) Notice: Subject to any disclaimer, the term of this patent is extended or adjusted under 35 U.S.C. 154(b) by 379 days.

(21) Appl. No.: 15/513,368

(22) PCT Filed: Oct. 20, 2014

(86) PCT No.: PCT/JP2014/077773
§ 371 (c)(1),
(2) Date: Mar. 22, 2017

(87) PCT Pub. No.: WO2016/063322
PCT Pub. Date: Apr. 28, 2016

(65) Prior Publication Data
US 2017/0307530 A1    Oct. 26, 2017

(51) Int. Cl.
*G01N 21/65* (2006.01)
*G01J 3/44* (2006.01)
*G01N 21/01* (2006.01)
*C12N 15/10* (2006.01)
*G01N 33/483* (2006.01)
*G01N 21/64* (2006.01)

(52) U.S. Cl.
CPC ......... *G01N 21/65* (2013.01); *C12N 15/1096* (2013.01); *G01J 3/44* (2013.01); *G01N 21/01* (2013.01); *G01N 33/4833* (2013.01); *G01N 2021/653* (2013.01); *G01N 2201/08* (2013.01); *G01N 2201/105* (2013.01)

(58) Field of Classification Search
None
See application file for complete search history.

(56) References Cited

U.S. PATENT DOCUMENTS

| | | | | |
|---|---|---|---|---|
| 5,866,430 A | * | 2/1999 | Grow | G01N 21/65 436/172 |
| 6,108,081 A | | 8/2000 | Holtom et al. | |
| 7,092,086 B2 | | 8/2006 | Knebel | |

(Continued)

FOREIGN PATENT DOCUMENTS

| JP | 2004-286579 A | 10/2004 |
|---|---|---|
| JP | 4257217 B2 | 4/2009 |

(Continued)

OTHER PUBLICATIONS

Dudovich, N. et al.; "Single-Pulse Coherently Controlled Nonlinear Raman Spectroscopy and Microscopy"; vol. 418; Aug. 2002; pp. 512-514.

(Continued)

*Primary Examiner* — Neil N Turk
(74) *Attorney, Agent, or Firm* — Miles & Stockbridge, P.C.

(57) ABSTRACT

In a multi-color CARS microscope, it has been difficult to accurately bring optical axes of pump light and Stokes light into correspondence and to stably acquire a spectral signal. Accordingly, in an optical analysis device, CARS light is generated from a sample by using a residual component of the pump light introduced to an optical waveguide and the Stokes light generated in an optical waveguide.

7 Claims, 14 Drawing Sheets

(56) References Cited

U.S. PATENT DOCUMENTS

| | | | |
|---|---|---|---|
| 2004/0057047 A1 | 3/2004 | Knebel | |
| 2005/0130164 A1 | 6/2005 | Akimoto et al. | |
| 2012/0122084 A1* | 5/2012 | Wagner | G01N 15/1436 |
| | | | 435/6.1 |
| 2013/0215422 A1 | 8/2013 | Kimura et al. | |
| 2015/0276483 A1 | 10/2015 | Mikami | |

FOREIGN PATENT DOCUMENTS

| | | |
|---|---|---|
| JP | 5100461 B2 | 12/2012 |
| JP | 2013-171154 A | 9/2013 |
| JP | 2014-503195 A | 2/2014 |
| WO | WO 2012/068287 A2 | 5/2012 |
| WO | WO 2014/061147 A1 | 4/2014 |

OTHER PUBLICATIONS

Tada, K. et al.; Single-Beam Coherent Anti-Stokes Raman Scattering Spectroscopy Using Both Pump and Soliton Stokes Pulses from a Photonic Crystal Fiber; Applied Physics Express 4; 092701; 2011.

Vartiainen, E. et al.; "Direct Extraction of Raman-Line Shapes from Congested CARS Spectra"; vol. 14; No. 8; Apr. 17, 2006; pp. 3622-3630.

Evans, C. L. et al.; Coherent Anti-Stokes Raman Scattering Spectral Interferometry: Determination of the Real and Imaginary Components of Nonlinear Susceptibility $X^{(3)}$ for Vibrational Microscopy; vol. 29; Issue 24; 2004; pp. 2923-2925.

* cited by examiner

OPTICAL ANALYSIS DEVICE AND BIOMOLECULAR ANALYSIS DEVICE

TECHNICAL FIELD

The present invention relates to achievement of high performance of an optical analysis device.

BACKGROUND ART

It goes without saying that an optical microscope is an indispensable observation tool in the fields of natural science, engineering, and industry. Especially in recent years, a microscope having higher performance using laser as an illumination light source has been becoming essential in advanced technology development. As a representative example, a coherent anti-Stokes Raman scattering (CARS) microscope (Patent Literatures 1 and 2) is known. The CARS microscope irradiates a sample with two types of laser beam, pump light and Stokes light, for observation of anti-Stokes light caused as a result of resonance of difference frequency between these lights with natural frequency of the sample molecule (hereinbelow referred to as CARS light). The microscope, which enables quantitative analytic observation of materials in the sample with the spectrum of the CARS light, attracts attention as non-invasive quantitative analysis means.

The operation principle of the CARS microscope will be described. CARS is light emission by third-order nonlinear polarization. To cause CARS, the pump light, the Stokes light, and probe light are required. In many cases, to reduce the number of light sources, the probe light is substituted with the pump light. In this case, induced third-order polarization is represented as $P(\omega)=(\chi_r^{(3)}(\omega)+\chi_{nr}^{(3)})E_P^2(\omega_P)E^*_S(\omega_S)$. Here $\chi_r^{(3)}(\omega)$ is a resonance section of the molecular vibrations of the third-order electric susceptibility, and $\chi_{nr}^{(3)}$ is a non-resonance section. Further, the electric field of the pump light and the probe light is represented with $E_P$, and the electric field of the Stokes light is represented with $E_S$. The non-resonance section has no frequency dependence. The asterisk attached to $E_S$ indicates a complex conjugate. The intensity of the CARS light is the square of the absolute value of $P(\omega)$. A mechanism to cause the CARS light will be described using an energy level diagram of the molecule shown in FIG. 15. Numeral 1401 denotes a vibration ground state of the molecule and 1402 denotes a vibration excited state. The pump light with a frequency of $\omega_P$ and the Stokes light with a frequency of $\omega_S$ are irradiated simultaneously. At this time, the molecule is excited via a virtual level 1403 to a vibration excitation level in the state 1402. When the molecule in the excitation state is irradiated with the probe light with a frequency of $\omega_P$, the molecule returns to the vibration ground state while emitting the CARS light with a frequency of $\omega_{AS}$ via the virtual level 1404. The frequency of the CARS light at this time is represented as $\omega=2\omega_P-\omega_S$.

Among the CARS microscopes, a microscope using a broadband light source as Stokes light for spectroscopic detection of generated CARS light is referred to as a multi-color CARS microscope (or multiplex CARS microscope). With the multi-color CARS microscope, it is possible to estimate Raman spectrum from the optical spectrum of the CARS light. In comparison with the method for detecting only a specific spectral component as in the case of Patent Literature 1 (this is referred to as monochromatic CARS or single CARS for the sake of convenience), the amount of acquired information is larger. Accordingly, this microscope is appropriate to more detailed analysis of the measurement object. The basic configuration of the multi-color CARS microscope is shown in 16. (The configuration is based on Patent Literature 2). The output from a short-pulse laser light source 1601 is split into two outputs with a beam splitter 1602. One output is introduced into an optical waveguide such as photonic crystal fiber 1603, and broadband light (referred to as super continuum light) is generated inside. After emission from the fiber, only a desired wavelength component (component having a longer wavelength than that of the pump light) is extracted from the super continuum light with a long-pass filter 1604. The extracted component is used as the Stokes light. The other pump light and the Stokes light are multiplexed with a dichroic mirror 1605 or the like. The multiplexed light is focused on a sample 1606 and irradiated, then CARS light is generated. The generated light is detected with a spectroscope 1607, and the spectrum is acquired.

CITATION LIST

Patent Literature

Patent Literature 1: U.S. Pat. No. 6,108,081
Patent Literature 2: Japanese Patent No. 5100461
Patent Literature 3: U.S. Pat. No. 7,092,086

Nonpatent Literature

Nonpatent Literature 1: Nirit Dudovich et al., Nature 418, 512-514 (2002)
Nonpatent Literature 2: Kazuhiro Tada and Naoki Karasawa, Applied Physics Express 4, 092701 (2011)
Nonpatent Literature 3: Erik M. Vartiainen et al., Optics Express, Vol. 14, Issue 8, pp. 3622-3630 (2006)
Nonpatent Literature 4: Conor L. Evans, et al., Optics Letters, Vol. 29, Issue 24, pp. 2923-2925 (2004)

SUMMARY OF INVENTION

Technical Problem

In the above-described multi-color CARS microscope, it is necessary that the position and angle of the optical axes of the pump light and the Stokes light irradiated on the sample accurately correspond with each other. Slight shift between them seriously reduces the generation efficiency of the CARS light. However, in the configuration where the pump light and the Stokes light, passing through spatially different optical paths, are multiplexed, the optical axes of the pump light and the CARS light gradually shift due to environmental temperature change or time deformation of the device. Accordingly, it is difficult to stably acquire data. This problem is not only a problem of the multi-color CARS microscope but is a common problem to most of the CARS microscopes including the monochromatic CARS microscope. As an exceptional case, in Patent Literature 3, two wavelength components of super continuum light, generated by introducing the pump light into a microstructure fiber (it has the same meaning as the photonic crystal fiber), are extracted with a wavelength filter and used as the pump light and the Stokes light. Since the pump light and the Stokes light are always coaxial with each other, the optical axes stably correspond with each other. In the present embodiment using the monochromatic CARS microscope, it is difficult to acquire spectrum information. It remains problematic to stably acquire the signal in the multi-color CARS microscope.

Further, according to Nonpatent Literatures 1 and 2, the pump light and the Stokes light are generated by shaping a very short pulse (within about 50 fs) time waveform with a pulse shaper having a diffraction grating, a spatial optical modulator and the like. The optical axes of the pump light and the Stokes light always correspond with each other. However, the laser light source having a pulse width within about 50 fs is currently limited to mode-locked laser. The device is large and expensive, and further, the pulse shaper has a complicated structure and is also expensive. The entire device is large, complicated and expensive.

In view of the above-described problems, the object of the present invention is to provide an optical analysis device having a simple configuration, to enable stable sample analysis for many hours, and a biomolecular analysis device to which the optical analysis device is applied.

Solution to Problem

In Patent Literature 2, the major part of the pump light introduced to the photonic crystal fiber is converted to the super continuum light. Accordingly, upon emission from the fiber, the intensity of the wavelength component of the pump light is seriously lowered. For this reason, in Patent Literature 2, the pump light which does not pass through the photonic crystal fiber is multiplexed with the Stokes light outside the fiber. On the other hand, the inventors have an idea of utilizing the pump light component passing through the photonic crystal fiber as pump light for CARS light generation. The inventors have found it possible to efficiently utilize the pump light by appropriately setting the length of the photonic crystal fiber. With this configuration, the pump light and the Stokes light are always coaxial with each other, and it is possible to stably perform data acquisition in the multi-color CARS microscope.

More particularly, the following means is used.

(1) An optical analysis device includes: a short-pulse laser light source such as microchip laser; an optical waveguide such as photonic crystal fiber that generates super continuum light by photoexcitation; a collecting optical system such as an aspherical lens that collects and introduces a light beam from the light source to the optical waveguide; a filter such as a long-pass filter that passes light emitted from the optical waveguide and eliminates a wavelength component shorter than a wavelength of the light beam from the light source; a second collecting optical system such as an objective lens that collects the light beam passed through the filter to a sample; and a spectroscope that detects CARS light generated from the sample.

With this configuration, it is possible to detect the CARS light more stably in comparison with the conventional art.

(2) In (1), the optical waveguide is photonic crystal fiber. With this configuration, the super continuum light is generated simply, and the configuration is simplified.

(3) In (2), the length of the photonic crystal fiber is within 1 m. With this configuration, it is possible to efficiently generate the CARS light with a simple configuration.

(4) An optical analysis device includes: a short-pulse laser light source such as titanium-sapphire laser that has output with a pulsewidth within 500 femtoseconds; an optical waveguide such as photonic crystal fiber that generates super continuum light by photoexcitation; a collecting optical system such as an aspherical lens that collects and introduces a light beam from the light source to the optical waveguide; a band-pass filter that passes light emitted from the optical waveguide, and passes a spectral component as a part of spectral components of the light beam from the light source and a wavelength component longer than a spectrum of the light beam from the light source; a second collecting optical system such as an objective lens that collects the light beam passed through the filter to a sample; and a spectroscope that detects CARS light generated from the sample.

With this configuration, it is possible to realize high generation efficiency of the super continuum light from the optical waveguide, and to shorten the length of the waveguide. Further, it is possible to realize downsizing and simplification of the device configuration.

(5) An optical analysis device includes: a short-pulse laser light source such as titanium-sapphire laser; an optical waveguide such as photonic crystal fiber that generates super continuum light by photoexcitation; a collecting optical system such as an aspherical lens that collects and introduces a light beam from the light source to the optical waveguide; a band-pass filter that passes light emitted from the optical waveguide, passes a spectral component as a part of spectral components of the light beam from the light source and a wavelength component longer than a spectrum of the light beam from the light source, and partially passes a wavelength component shorter than the spectrum of the light beam from the light source; a collecting optical system that collects the light beam passed through the filter to the sample; a second collecting optical system such as an objective lens that collects the light beam passed through the filter to the sample; and a spectroscope that detects CARS light generated from the sample.

With this configuration, the detected signal is amplified with the effect of heterodyne detection. It is possible to stably acquire data with high sensitivity.

(6) A biomolecular analysis device includes: a short-pulse laser light source such as microchip laser; an optical waveguide such as photonic crystal fiber that generates super continuum light by photoexcitation; a collecting optical system such as an aspherical lens that collects and introduces a light beam from the light source to the optical waveguide; a filter that passes light emitted from the optical waveguide and eliminates a wavelength component shorter than a wavelength of the light beam from the light source; a sample holder that holds a plurality of cells as a sample; an observation unit such as a differential interference microscope that observes the cell held with the sample holder; an irradiation optical system that collects and irradiates the light beam passed through the filter to the cell held with the sample holder; a spectroscopic unit that acquires spectrally coherent anti-Stokes Raman scattering light generated from the cell by light irradiation; a detection unit such as a CCD camera that detects the spectral light acquired with the spectroscopic unit; an irradiation control unit that controls a light irradiation position to the cell with the irradiation optical system; cell destruction means for destroying the cell held with the sample holder; and a biomolecular capture device that captures a biomolecule in the cell discharged from the cell by destruction.

With this configuration, it is possible to analyze a biological sample at a high speed and with high accuracy.

(7) In (6), the cell destruction means destroys the cell by laser beam irradiation. With this configuration, the device is downsized.

(8) The biomolecular analysis device further includes: a memory for storing the spectrum outputted in (6) and data analyzed using the biomolecule capture device, associated with each other. With this configuration, it is possible to efficiently manage the optical spectrum information of the biomolecule, and to realize more efficient data analysis.

Advantageous Effects of Invention

According to the present invention, it is possible to provide an optical analysis device, having a simple configuration, capable of data acquisition more stably in comparison with the conventional art.

Other objects, the features and advantages of the present invention may be clearer with the following description of the embodiments.

DESCRIPTION OF EMBODIMENTS

Hereinbelow, embodiments of the present invention will be described with reference to the drawings.

First Embodiment

Figure 1:
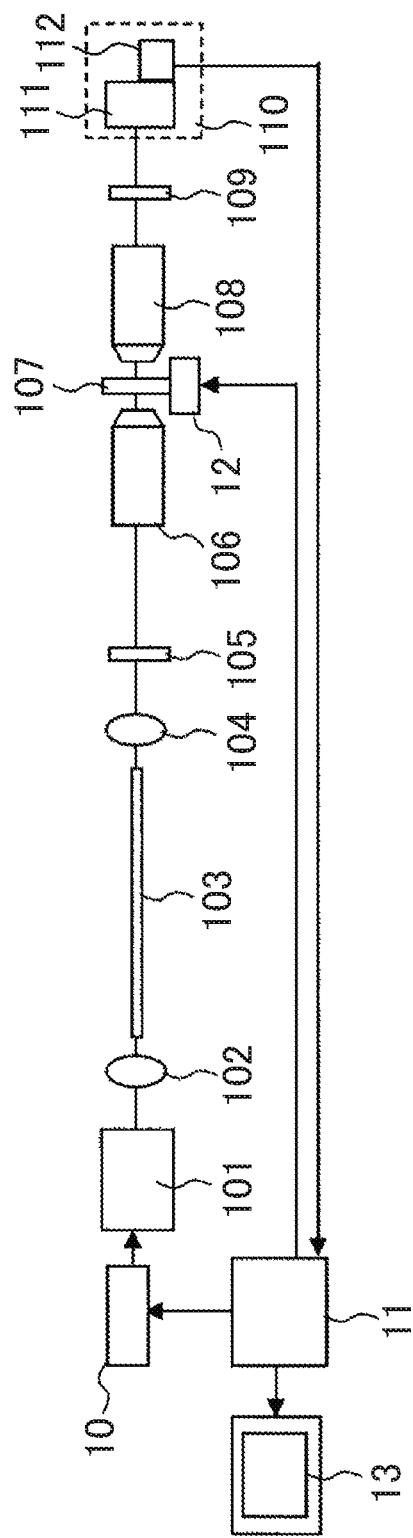
FIG. 1 is a schematic diagram showing a configuration example of a CARS microscope according to the present invention.

FIG. 1 is a schematic diagram showing a basic configuration example of the optical analysis device according to the present invention. Hereinbelow, the operation of the present embodiment will be described in accordance with FIG. 1.

A laser beam, emitted from a light source, light-emission controlled through a driver 10 based on a command from a computer 11, i.e., a short-pulse laser light source 101 (with a center wavelength of 1064 nm, a pulse width of 900 ps, a repetition frequency of 30 kHz, and an average output of 200 mW), is coupled to a photonic crystal fiber 103 with a collecting lens 102. Then broadband super continuum light is generated in the fiber. The generated super continuum light is collimated with a collimator lens 104, then enters a long-pass filter 105, and components having shorter wavelength than that of the short-pulse laser light source are cut off. That is, the light transmitted through the long-pass filter 105 has a laser light source wavelength component used as pump light and a component having longer wavelength than that of the pump light used as a Stokes light component. The light beam is condensed to one point of a sample 107 with an objective lens 106 (with an NA of 0.9 and 40 times magnification), and CARS light reflecting resonance oscillation of the molecule existing in the light condensed position of the sample is generated. The CARS light is collimated with a condenser lens 108 (with an NA of 0.65). The light passes through a short-pass filter 109, where the pump light and the Stokes light as coaxial components are cut off. Then the light enters a spectroscope 110, where the light is diffracted with a spectroscopic unit 111, then detected with a detection unit 112 separately by wavelength, and the spectrum is outputted as a detection signal.

Figure 2:
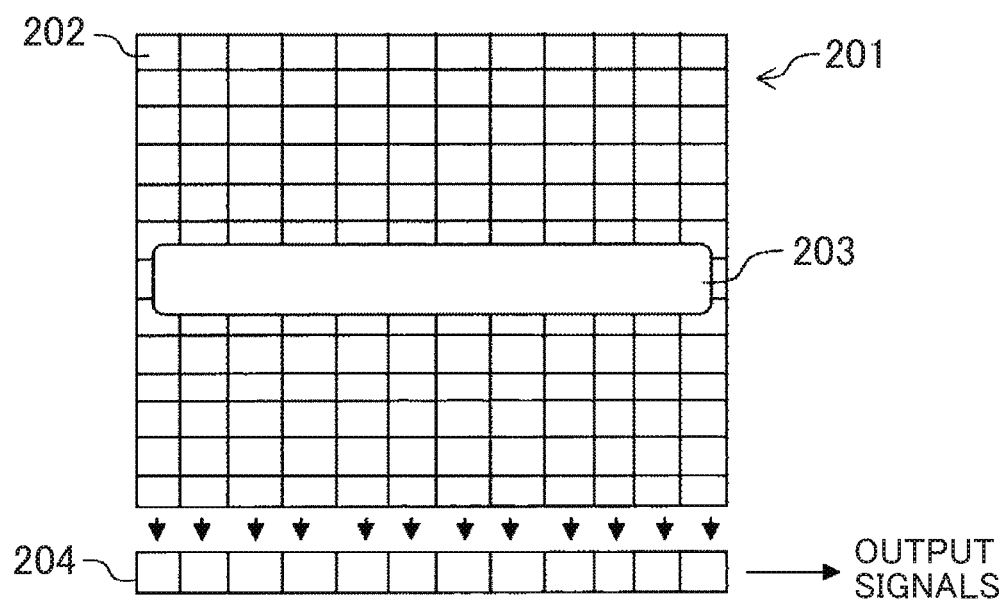
FIG. 2 is a schematic diagram of a light receiving unit of a CCD camera.

The detection operation of the spectroscope 110 will be described here. The spectroscope 110 has a spectroscopic unit 111 to diffract incident light in different directions by wavelength with a diffraction grating, and a detection unit 112 to detect the light diffracted with the spectroscopic unit 111 using a one-dimensional or two-dimensional detector array (a CCD camera, a CMOS camera or the like). In the present embodiment, a CCD camera is used as the detection unit 112. As shown in FIG. 2, a light-receiving unit 201 of the camera is a two-dimensional array of pixels 202. The light diffracted with the spectroscopic unit 111 enters the light receiving unit as a horizontally elongated beam 203 where the wavelength differs in accordance with horizontal position. The CCD camera of the detection unit 112 is controlled from, the outside to an exposure status during a predetermined period of time, i.e. a status where each pixel is exposed with the incident light, to convert the incident light into an electric charge, and the electric charge is stored. After the completion of the exposure, the total electric charge amount stored in the longitudinal pixel array is transferred to a buffer 204 (full vertical binning). The electric charge of the buffer 204 is outputted as a serial signal to the outside. Accordingly, the output signal is proportional to the intensity of the incident light by each wavelength, i.e. a spectral signal of the incident light.

In the present embodiment, an XYZ stage 12 holding a sample 107 is driven to scan the light condensing position of the pump light and the Stokes light to the sample three-dimensionally or two-dimensionally, to acquire a spectral signal upon change of the light condensing position. Accordingly, spectral data from each position of the sample is finally acquired. Further, an image by spectrum is acquired by mapping a particular spectral value of each point (hyper spectral imaging).

Figure 3:
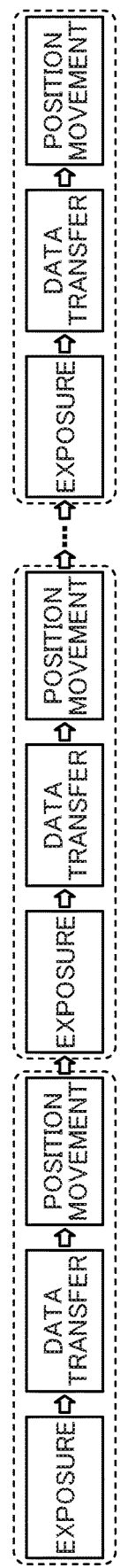
FIG. 3 is a sequence diagram of a data acquisition operation.

The sequence of data acquisition in the present embodiment is as shown in FIG. 3. The operations of exposure, data transfer and position change are repeated by the number of data points. Note that the order of the data transfer and the position change may be exchanged, or the operations may be performed simultaneously.

After the data acquisition, each measured spectral data piece is subjected to data processing such as the maximum entropy method, and the Raman spectrum is restored. The user acquires the density distribution of the measurement object matter and the total molecule amount included in the entire sample by reading each resonance peak value of the restored Raman spectrum, to use them in various analyses. Note that it may be configured such that in accordance with purpose, the maximum entropy method is not performed but a peak value of raw spectral data is read and used in analysis.

Figure 4:
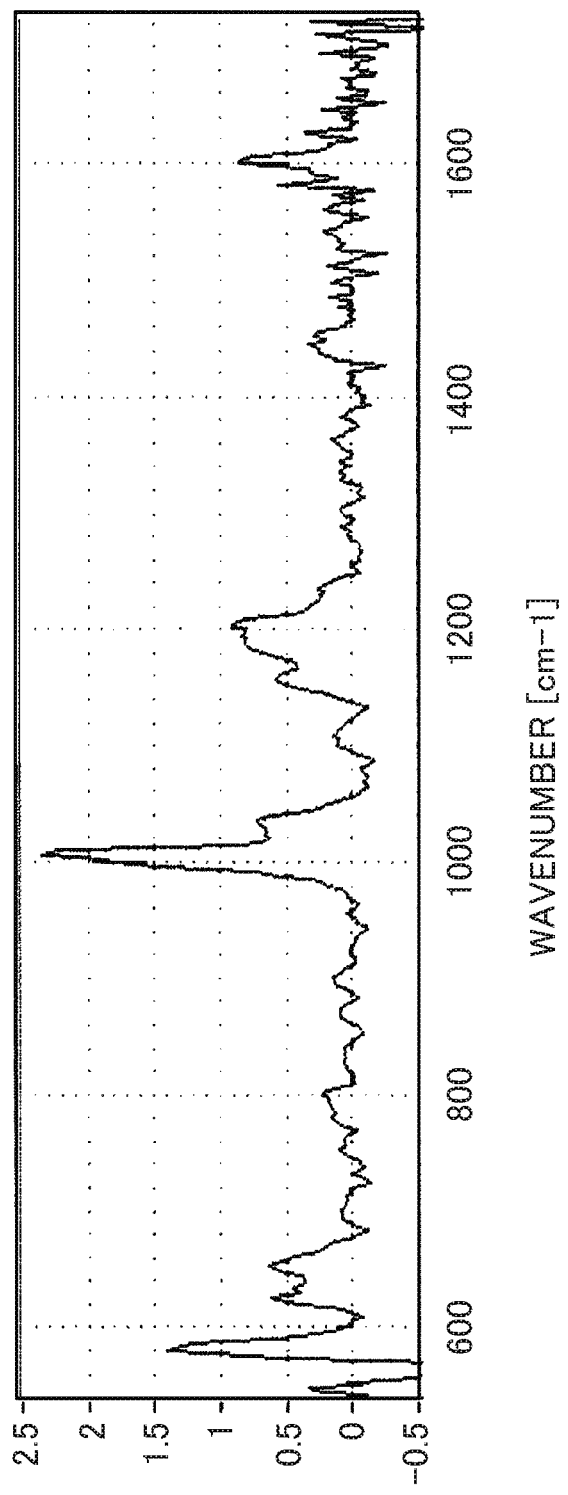
FIG. 4 illustrates a Raman spectrum of a polystyrene bead reconstructed with data acquired in accordance with the present invention.

FIG. 4 shows, as an experimental result of the present embodiment, the result of restoration of the Raman spectrum of a polystyrene bead. The length of the photonic crystal fiber is 0.5 m. The sample is a polystyrene bead soaked in water. The Raman spectrum was restored by applying the maximum entropy method to the spectrum of the CARS light acquired from the polystyrene bead, standardized by dividing the CARS light spectrum acquired from water, and further, by performing interpolation processing to correct the phase offset. (The details of these data processing steps are described in Nonpatent Literature 3.) As a result, the Raman spectrum characteristic of the polystyrene was restored. Similar data was applied to the photonic crystal fiber having the lengths of 0.65 m and 1 m, and as a result, a similar spectrum was restored. These results guarantee the feasibility of the present invention. Note that there was a tendency that when the fiber was longer, the signal level was lowered. When the length was 1 m, the signal level was very weak. That is, it is desirable that the length of the fiber is within 1 m. On the other hand, when the fiber is extremely short, the super continuum, light is not generated. It is necessary that the length of the fiber is at least 10 cm.

The role of the long-pass filter 105 in the present embodiment will be described here again since it is important. The long-pass filter 105 has a role of cutting a part of wavelength band of the CARS light generated from the sample 107, from the super continuum light, generated from the photonic crystal fiber 103. The super continuum light generally has intensity far higher than that of the CARS light generated from the sample. When it is detected with the spectroscope, it appears as a large offset component in the CARS light to be detected, which causes difficulty in correct detection of the CARS light. Accordingly, it is necessary to selectively eliminate the wavelength component with the long-pass filter for correct data acquisition.

Here the difference between the present embodiment and the configuration of Patent Literature 3 will be clarified. The most important difference is that a multi-color CARS microscope is used in the present embodiment while a monochromatic CARS microscope is used in Patent Literature 3. Accordingly, in the present embodiment, the long-pass filter 106 is used while Patent Literature 3 is based on the use of a filter to extract two wavelength components of the super continuum light. That is, in the present embodiment, all the components of the super continuum light having a wavelength longer than that of the pump light are irradiated to the sample. As a result, it is possible to acquire the spectral information of the CARS light, which cannot be acquired with the configuration of Patent Literature 3. Note that in the configuration of Patent Literature 3, the CARS light is detected by using a spectroscope. However, the detected CARS light is almost monochrome, and the spectrum of the CARS light emitted from the sample is not acquired.

Figure 5:
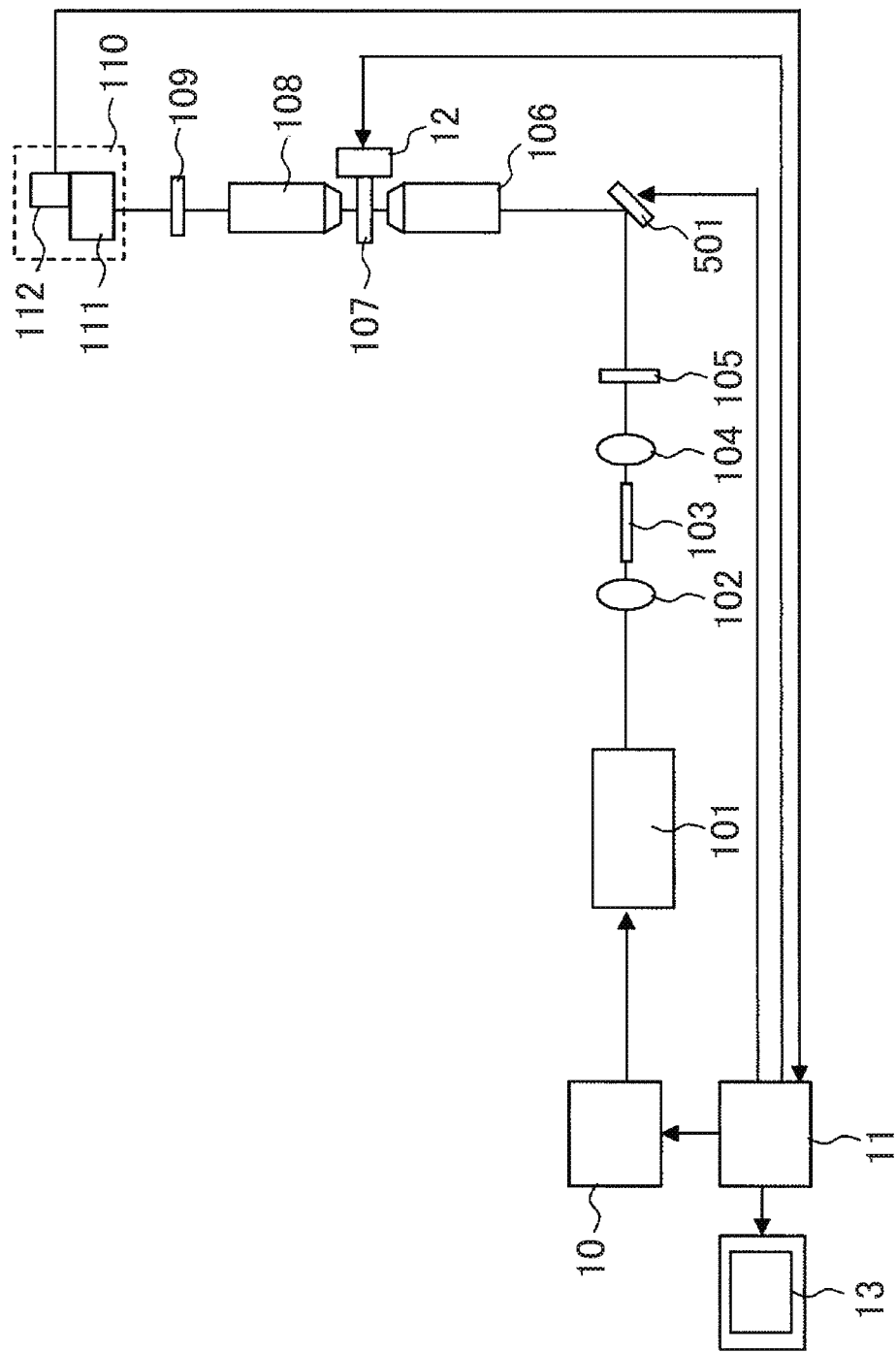
FIG. 5 is a configuration diagram, when a scan mirror is used.

In the present embodiment, the XYZ stage 12 is used as an irradiation control unit to control a light irradiation position to the sample with the irradiation optical system, and the sample position is scanned for scanning of measuring point. However, the control of light irradiation position with the irradiation control unit is not limited to this method. For example, as an irradiation control unit, a scan mirror, to scan the incident angle of the pump light and the Stokes light to the sample by external control, such as a galvanometer mirror or a MEMS mirror, may be used. Otherwise, the position of the objective lens 106 may be scanned. Otherwise, a combination of the above-described methods may be used. An example of scanning of an axis specially using a galvanometer mirror will be described using FIG. 5. In this case, a galvanometer mirror 501 is inserted between the long-pass filter 105 and the objective lens 106. The pump light and the Stokes light are reflected, then enter the objective lens 106. Note that the installation angle of the galvanometer mirror is controlled by external control from the computer 13. With this configuration, it is possible to control the angle of the light beams of the pump light and the Stokes light. The pump light and the Stokes light, the angles of which are changed with the galvanometer mirror, are condensed in a position of the sample different from that before the angle change, and the CARS light also generated in the light-receiving surface of the CCD camera enters a different position. The angular scan direction of the galvanometer mirror is set such that the position of the CARS light is changed in the longitudinal direction in FIG. 2 (the direction vertical to the diffraction direction) in the light-receiving surface of the CCD camera. In this case, the beam 203 of the CARS light moves in the vertical direction. As described above, since data accumulated in the vertical direction is outputted upon data acquisition, the positional change of the beam has no influence on the output signal. The other axis is scanned by using the XYZ stage 12. This operation is the same even when other scan mirror such as an MEMS mirror is used. These scan mirrors are generally operated at a higher speed in comparison with the XYZ stage or the like. It is possible to perform faster measurement by applying these mirrors.

Figure 6:
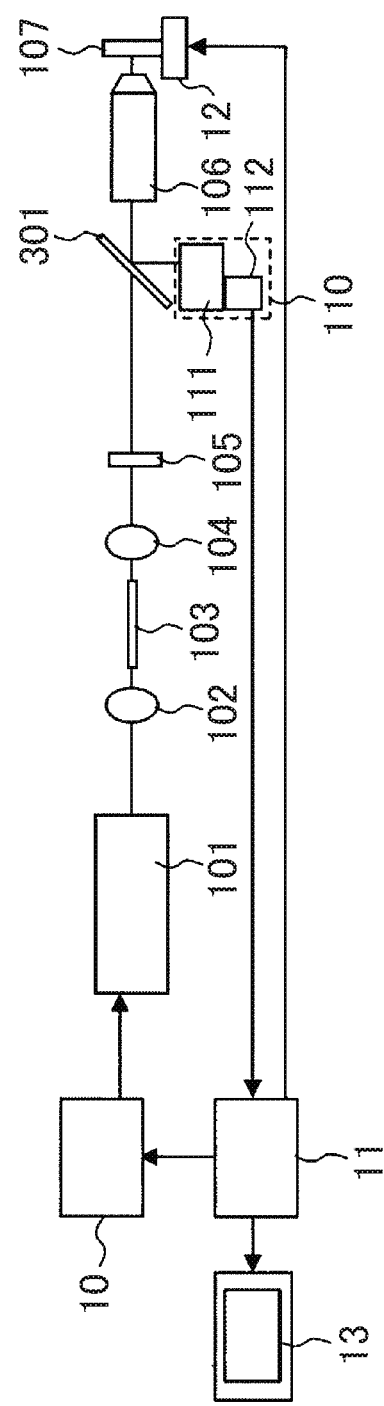
FIG. 6 is a configuration diagram of an optical analysis device to detect backscatter of CARS light.

Further, in the present embodiment, the spectroscope is provided on the side opposite to the incident side of the pump light and the Stokes light on the sample. It may be configured such that the spectroscope is provided on the same side, and the backscatter light from the sample is detected as parallel light with the spectroscope using the objective lens 106. In this case, as shown in the schematic diagram of FIG. 6, the pump light, the Stokes light and the CARS light are coaxial with each other. Accordingly, it is necessary to separate the CARS light from the pump light and the Stokes light with the beam splitter 301 or the like.

In the present embodiment, it is assumed that the CCD camera is used as the detector. However, the detector is not limited to the CCD camera. It is possible to attain the same advantage when a CMOS camera or a line sensor as a one-dimensional detector array.

In the present embodiment, it is possible to perform imaging by outputting a spectrum which differs by sample position. It goes without saying that the same method is applicable to spectroscopic analysis means for spectral analysis of a single or plural points of a sample.

Further, it is possible to substitute another optical waveguide to generate super continuum light source for the photonic crystal fiber 103. For example, tapered fiber or core-shaped comparatively small single mode fiber may be used. Further, the form of the optical waveguide is not necessarily fiber. An optical waveguide having a mode field diameter of 10 um or smaller mounted on the substrate may be used.

It is necessary that the pulse laser light source in the present embodiment has pulse energy to sufficiently generate super continuum light. As specifications required for this purpose, a laser light source having a pulse width within 5 ns, a peak power of 1 kW or higher, and an average output of 10 mW or higher is desirable. As laser fulfilling such condition, mode-locked titanium-sapphire laser or the like is given.

The long-pass filter in the present embodiment is inserted for the purpose of cutting off components of wavelengths shorter than the wavelength of the short-pulse laser light source in the super continuum light so as to sufficiently reduce the background level upon detection of the CARS light. Accordingly, it is desirable to set, as the degree of cutting off in the band to be cut off, the components of the wavelengths shorter than the wavelength of the short-pulse laser light source in the super continuum light are at about the same or lower level than that of the CARS light upon detection with the spectroscope. In the present embodiment, it is determined that an OD 6 (i.e., attenuation rate of $10^{-6}$) filter is sufficient. However, it is necessary to use an appropriate filter in accordance with signal amount.

It is assumed that the optical filters in the present embodiment such as the long-pass filter and the short-pass filter are a bulk type filter having a dielectric multilayer. However, the form of the optical filter is not limited to this filter. For example, a fiber-type filter such as a Fiber Bragg Grating may be used. Or a method of separating spatially different wavelength components with a diffraction grating or a prism pair and cutting off unnecessary components with a knife edge or the like (this configuration is shown in Nonpatent Literature 1) may be used.

Second Embodiment

Figure 7:
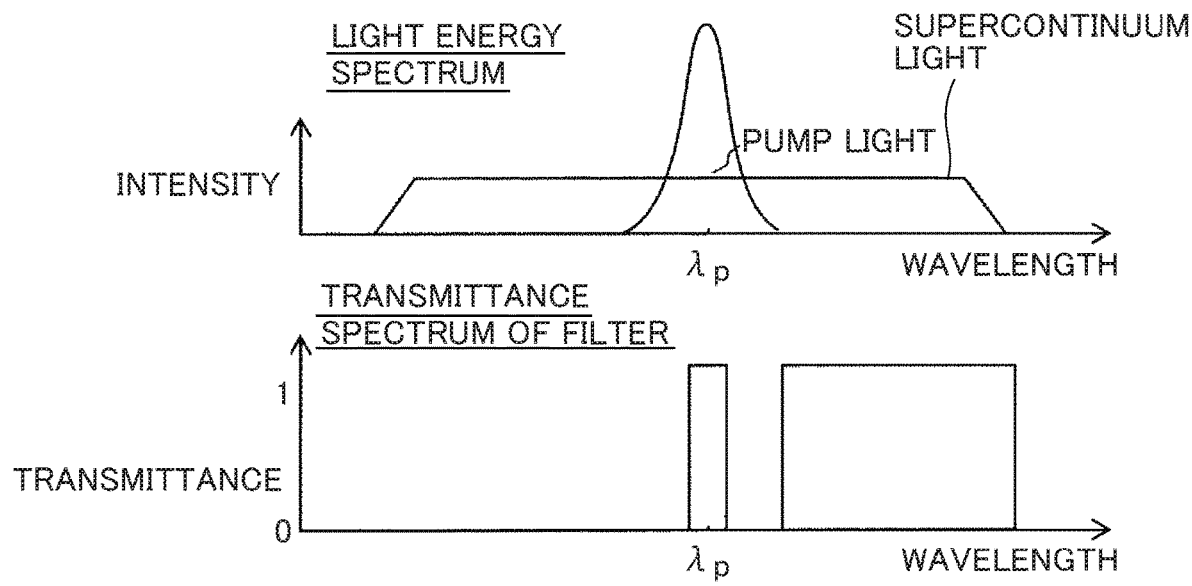
FIG. 7 illustrates transmission characteristics of a band-pass filter in a second embodiment of the present invention.

The present embodiment is an embodiment using femtosecond laser as a light source. The configuration of the present embodiment is basically the same as that in FIG. 1. The difference is that the laser light source is the femtosecond laser and that the long-pass filter 106 is replaced with a special band-pass filter. (Note that the femtosecond laser means laser having a pulse width within 500 fs.) This band-pass filter has a transmittance characteristic as shown in FIG. 7. It passes a narrow spectral component as a part of the pump light and components of the super continuum light having a wavelength longer than that of the pump light. When the spectral width of the pump light is wide, the wavelength resolution of the spectrum of the CARS light is lowered. Accordingly, the spectrum of the pump light is narrowed with the filter in the present embodiment, to ensure a sufficient wavelength resolution. In the present embodiment, it is possible to efficiently generate the super continuum light by using the femtosecond laser, and to shorten the photonic crystal fiber. It is possible to simplify the configuration and realize cost reduction.

Third Embodiment

Figure 8:
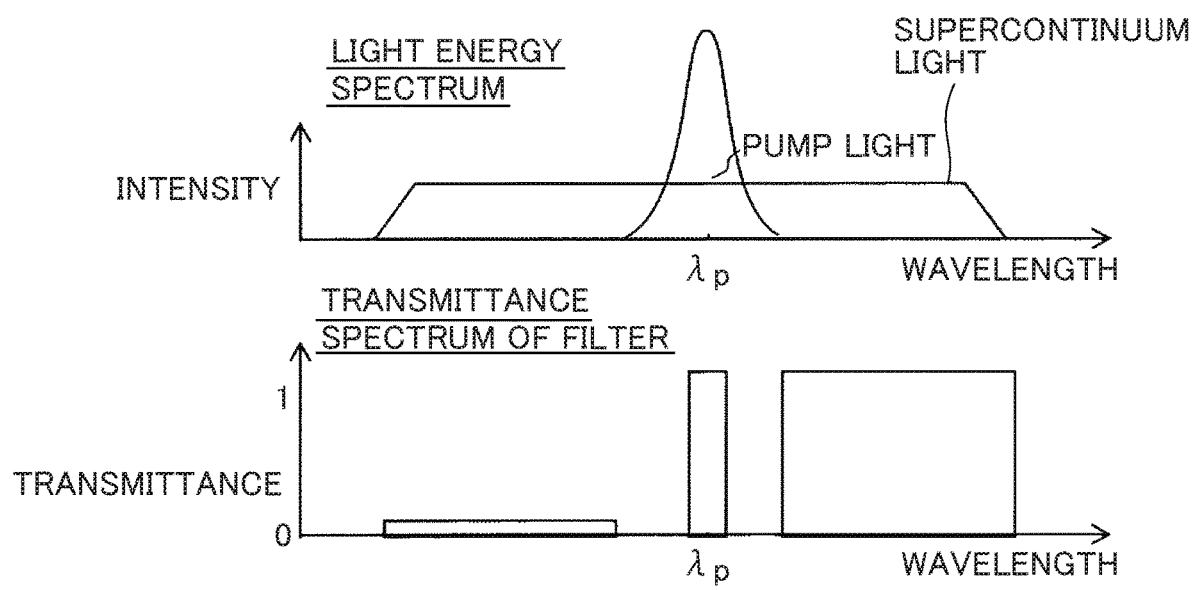
FIG. 8 illustrates the transmission characteristics of the band-pass filter in a third embodiment of the present invention.

The present embodiment is an embodiment to perform heterodyne detection with respect to the CARS light generated from the sample. In the present embodiment, in comparison with the second embodiment, only the transmission characteristics of the band-pass filter is different. As shown in FIG. 8, the transmission characteristics of the band-pass filter in the present embodiment has a slight transmittance for components of the super continuum light having a wavelength shorter than that of the pump light in addition to the transmission band of the filter in the second embodiment. The components interfere with the CARS light from the sample. The interfered light is detected with the spectroscope. The method of interfering detected light with other light (referred to as a local oscillator) and detecting the light in this manner is referred to as heterodyne detection. The heterodyne detection has advantages such as signal level amplification. (For example, in the CARS microscope, Nonpatent Literature 4 shows an example.) In the heterodyne detection, it is necessary that the optical axes of the local oscillator and the detected light (in the present embodiment, the CARS light generated from the sample) accurately correspond with each other. In the present embodiment, the local oscillator, the pump light and the Stokes light are always coaxial with each other. It is possible to stably acquire a signal.

Fourth Embodiment

The present embodiment is an embodiment of the biomolecular analysis device in which the optical analysis device according to the present invention is applied to single cell analysis, and an embodiment where a CARS spectrum is acquired as one form of cell analysis.

Figure 9:
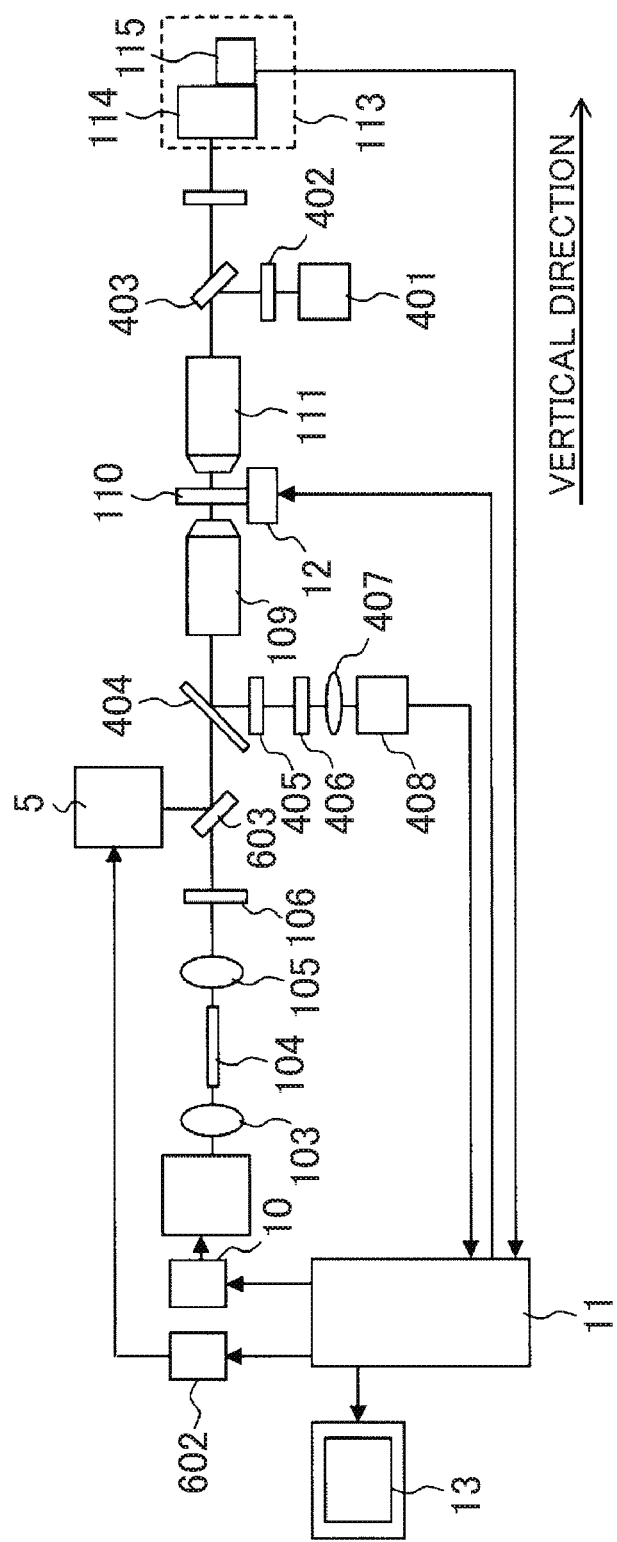
FIG. 9 is a schematic diagram showing a configuration example of the optical analysis device.
Figure 10:
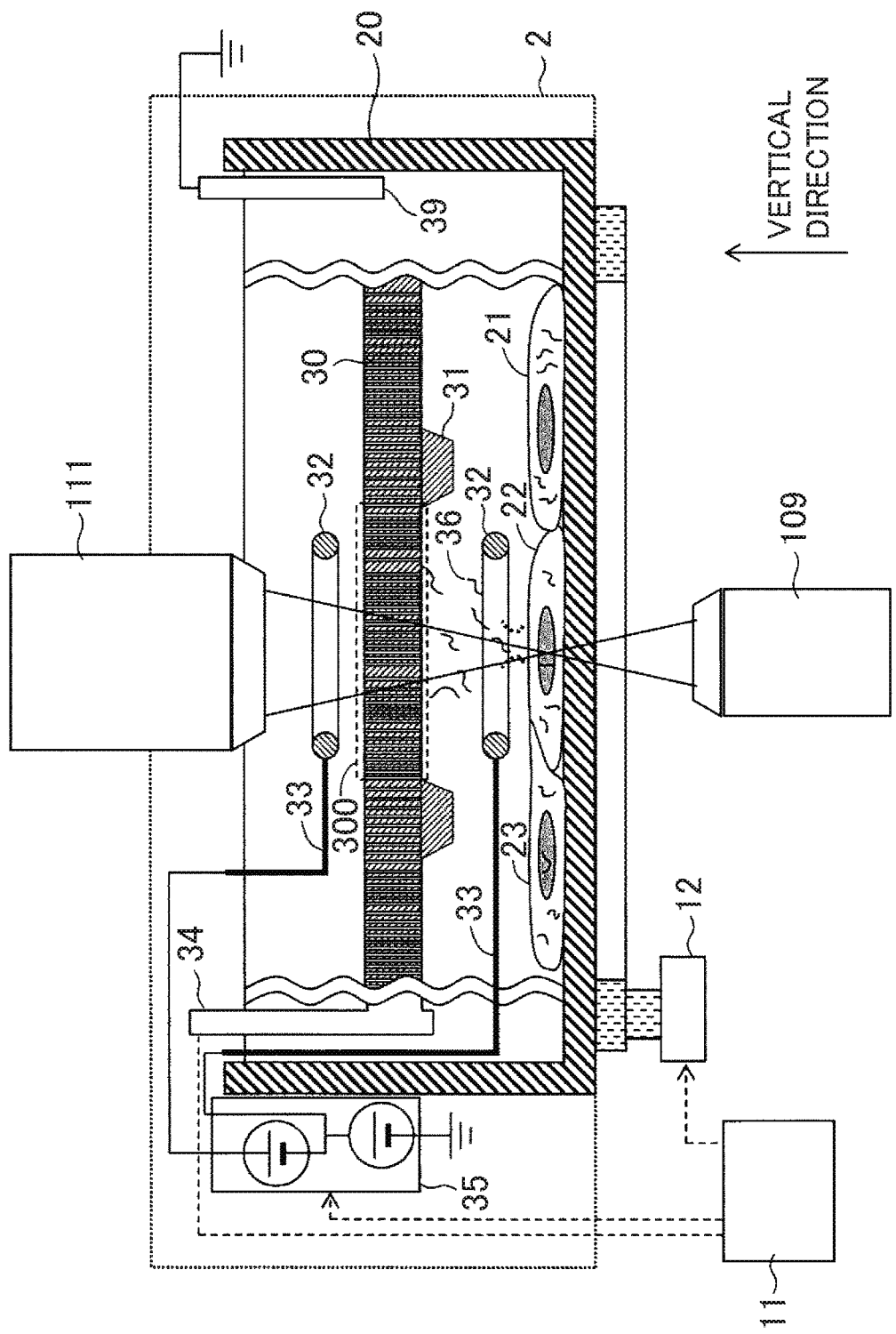
FIG. 10 is a schematic diagram showing another configuration example of the optical analysis device.

FIG. 9 and FIG. 10 are schematic diagrams showing configuration examples of the biomolecular analysis device according to the present embodiment. FIG. 9 is a schematic diagram showing an optical system part of the present device. FIG. 10 is a detailed diagram of peripheral part of a sample showing a configuration example of the biomolecule collecting system. FIG. 10 includes a biomolecule collecting system 2 to capture the mRNA of a cell as a sample for gene expression analysis. The computer 11 controls the optical system part and the biomolecule collecting system and performs data acquisition (Explanation of Optical System Part)

The optical system part of the device shown in FIG. 9 has, in addition to the configuration, a differential observation system, the cell destruction laser 5 (pulse laser having a wavelength of 355 nm, an average output of 2 W, and a repetition frequency of 5 kHz), a driver 602, and a dichroic mirror 603 to convert emission light from the laser 5 to light coaxial with the pump light and the Stokes light. The optical system part includes three functions, (1) acquisition of a differential interference microscope image, (2) acquisition of a CARS spectrum, and (3) cell destruction. The respective functions will be described below. Regarding (1), first, illumination light from the illumination 401 (halogen lamp) is passed through a Wollaston prism 402, reflected with a dichroic mirror 403, and focused with a condenser lens 111 on a sample 110. A differential interference image of the sample 110 is focused on an image pickup device such as a CCD camera 408 using the objective lens 106, a dichroic mirror 404, a Wollaston prism 405, a polarizer 406, and an imaging lens 407, thus an image of the sample is acquired. This configuration is the same as that of a well-known differential interference microscope. Note that the dichroic mirrors 403 and 404 are designed to reflect wavelengths in a visible light region of the illumination 401 (400 to 700 nm), but pass the pump light, the Stokes light, and the CARS light (all having a wavelength in a near-infrared region of 700 nm or longer). The mirrors have no influence on generation and detection of the CARS signal. The function of (2) is as described in the first embodiment. The function of (3) is a function of focusing emission light from the cell destruction laser 5 on the cell as an observation object with the objective lens 106, destroying the cell to discharge biomolecules such as an mRNA inside the cell to the outside. The discharged mRNA is captured and analyzed with the biomolecule collecting system 2 as described later.

(Explanation of Biomolecule Collecting System)

The biomolecule collecting system 2 shown in FIG. 10 has an array device with an array of regions to capture biomolecules such as the mRNA discharged from the cell. For example, it is possible to capture the mRNA in plural regions of the array device by single cell, and to construct a cDNA library by performing reverse transcription reaction with the array device. In the present embodiment, the array device is constructed with a transparent porous membrane in which a large number of through holes are formed vertically to the surface. Hereinbelow, this will be referred to as a pore array sheet 30. Further, the array sheet where the cDNA library is formed in the pore array sheet 30 will be referred to as a cDNA library pore array sheet.

In the present embodiment, as the pore array sheet 30, an aluminum-oxide porous membrane having a thickness of 80 µm and a size of 2 mm×2 mm where a large number of through holes having a diameter of 0.2 µm are formed by anodic oxidation is used. In the pore array sheet 30, it is possible to form a separation wall 31 to separate the regions to capture the biomolecules. The separation wall 31 is formed by, e.g., semiconductor process using polydimethylsiloxane (PDMS). The separation wall having a thickness of about 80 µm is tightly attached to the pore array sheet 30.

Figure 11:
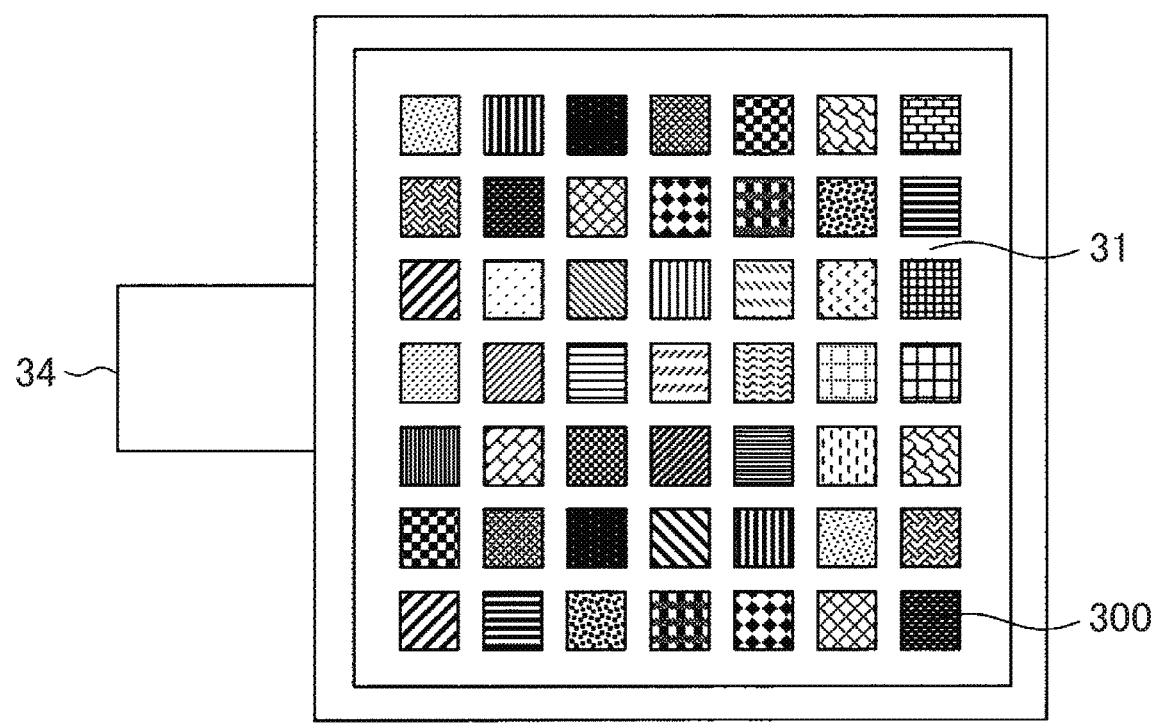
FIG. 11 is a top view of a pore array sheet.

FIG. 11 is a top view of the pore array sheet 30. In the pore array sheet 30 (having a size of 2 mm×2 mm and a thickness of 80 µm), a region 300 to capture a large number of biomolecules, e.g., the mRNA is formed. Here as the size of the region 300, one side is 100 µm, and the interval is 80 µm (provided at a period of 180 µm). It is possible to freely set the size of the region 300 from about 1 µm to 10 mm in correspondence with amount of biomolecules to be captured and in-plane diffusibility (molecule size).

As the array device, in addition to the pore array sheet 30 of porous membrane formed by anodic oxidation of aluminum, a sheet with a large number of through holes formed by anodic oxidation of other material such as silicon may be used. Further, it may be configured such that the array device is constructed by providing a large number of through holes in a thin film of silicon oxide or silicon nitride using semiconductor process.

As shown in FIG. 10, as means for guiding the biomolecules discharged from the cell to a particular region in the pore array sheet 30 by electrophoresis, a loop-shaped platinum electrode 32 is joined to the end of a shield wire 33. The diameter of the wire of the platinum electrode 32 is 30 µm. The wire is folded to two, then the lead joints are twisted to one, and the loop side is processed to a circle having a diameter of 100 µm. Two of such electrodes are made, and provided to hold the pore array sheet 30 between them, and a direct current of 1.5 V is applied from a power supply 35 to the electrodes. Since a discharged mRNA 36 has a negative electrical charge, the upper platinum electrode 32 is used as a positive electrode. Note that a reference electrode 39 of silver-silver chloride is provided, and 0.2 V is applied to the lower platinum electrode 32. With this operation, it is possible to guide the mRNA 36 by electrophoresis to the inside of the region 300 to capture the biomolecule. Further, to further improve biomolecule capture efficiency, it may be configured such that the loop diameter of the upper platinum electrode 32 is 50 µm to realize condensation of the mRNA by lateral electrophoresis. In this case, the diameter of the wire is 10 µm.

(Explanation of Operation Flow)

Figure 12:
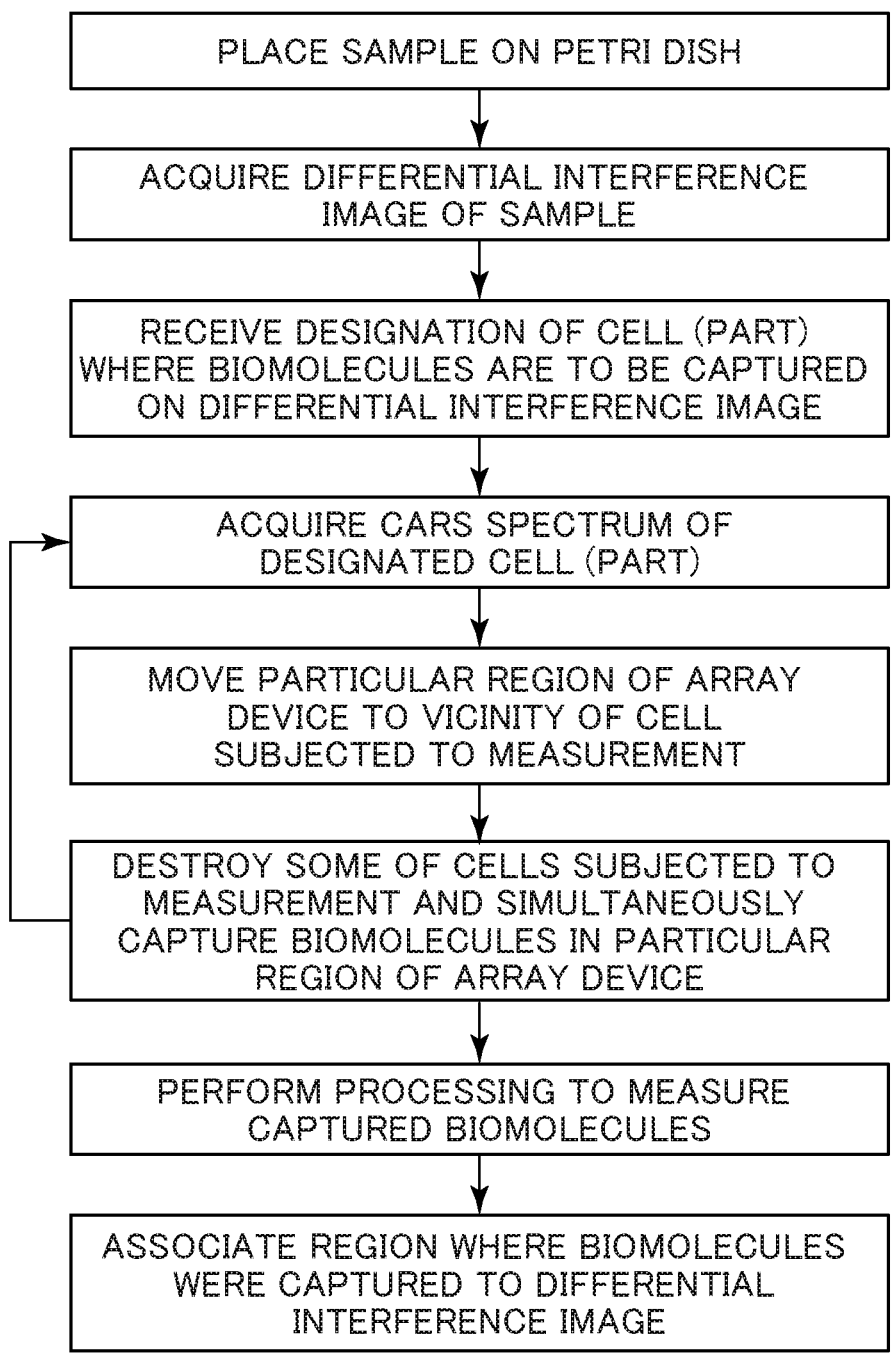
FIG. 12 is a flowchart explaining an operation of a biomolecular analysis device.

Next, an operation flow of the biomolecular analysis device according to the present embodiment will be described. FIG. 12 shows an example of the flowchart.

First, a sample of adhesive systems cultured cells 21, 22 and 23 is placed on a petri dish 20. In the embodiment, since the measurement object is a cultured cell, it is previously cultured using the petri dish 20 such that the cell as the measurement object is attached to the bottom surface. When the sample is a frozen section, it is placed on the petri dish 20. Otherwise, plural cells three-dimensionally provided in gel may be used as a sample. Next, a differential interference image of the cell group as the object is acquired using the microscope system. Then biomolecules are obtained, and the user determines a cell as an object of measurement. Next, the computer 11 receives input of information on the cell as the object of measurement or the cell part from the user. Generally, the user designates plural cells as measurement objects in many cases. In such a case, the computer 11 determines the order of cells to capture the biomolecules. First, the computer drives the XYZ stage 12 such that the first object cell is provided in the center of the field of view. Here the CARS spectrum of the cell provided in the center of the field of view is acquired by the method described in the first embodiment. Then quantitative value data, acquired by the method described in the first embodiment from the acquired spectrum, is stored in the computer 11.

Next, the computer 11 moves a particular region of the pore array sheet 30 (for example, the region 300 at address (1, 1), using the XYZ stage 34, to the vicinity of the cell of which the CARS spectrum has been acquired (in the example of FIG. 10, immediately above the cell. In the present embodiment, the distance between the lower surface of the pore array sheet 30 and the petri dish 20 is set to be 300 µm. This distance is variable in accordance with type of collected biomolecule or electrode structure. For example, the distance about from 1 µm to 10 mm is appropriate. The movement of the pore array sheet 30 with, the XYZ stage 34 is automatically performed with the computer 11 in accordance with a prepared program. When the completion of movement has been checked with the computer 11, a voltage is applied to the platinum electrode 32 for electrophoresis, and at the same time, to destroy the cell membrane as the measurement object, the cell is irradiated with the laser beam from the cell destruction laser light source 5. Here, it may be configured such that, for example, the irradiation time is 10 seconds and the electrophoresis driving time is 60 seconds.

When the destruction of one cell and the capture of the biomolecules in the cell have been completed, the computer 11 drives the XYZ stage 12 to position the registered second object cell to the center of the field of view. Thereafter, the CARS spectrum of the second cell is acquired, and the data is stored in the computer 11. Next, the computer 11 drives the XYZ stage 34 to move a particular region of the pore array sheet 30 (for example, the region 300 at address (1, 2)) to the vicinity of the second object cell (in the configuration example of FIG. 10, immediately above the cell). Then, the second cell registered with the computer 11 is irradiated with the laser beam from the cell destruction laser 5. At this time, as in the case of the above description, the voltage is applied to the platinum electrode 32 at the same time. Thereafter, the above-described CARS spectrum acquisition is performed on the sequentially designated cell, then cell is destroyed, then after the capture of the biomolecules in the cell in the particular region 300 of the pore array sheet 30, processing to measure the captured biomolecules is performed. Finally, a part of the differential interference image corresponding to the destroyed cell, the region 300 of the pore array sheet 30 in which the biomolecules have been captured, the acquired CARS spectrum and the quantitative value acquired from the spectrum, are associated with each other, and presented to the user.

Here the number of destroyed cells is one. However, when more rough resolution data is to be acquired, the mRNAs discharged and electrophoresis-moved upon destruction of plural cells may be captured with respect to one region 300 on the array device. The destruction at that time may be simultaneously performed on the plural cells, or may be sequentially performed by one cell without moving the array device. Further, in the present embodiment, in the flow, the acquisition of the CARS spectrum and the capture of the biomolecules are sequentially performed with respect to different cells. The flow may be configured such that, for example, after the acquisition of the differential interference image of the sample, all the CARS spectra of the object cells are measured, then the respective cells are sequentially destroyed and the biomolecules are captured.

Figure 13:
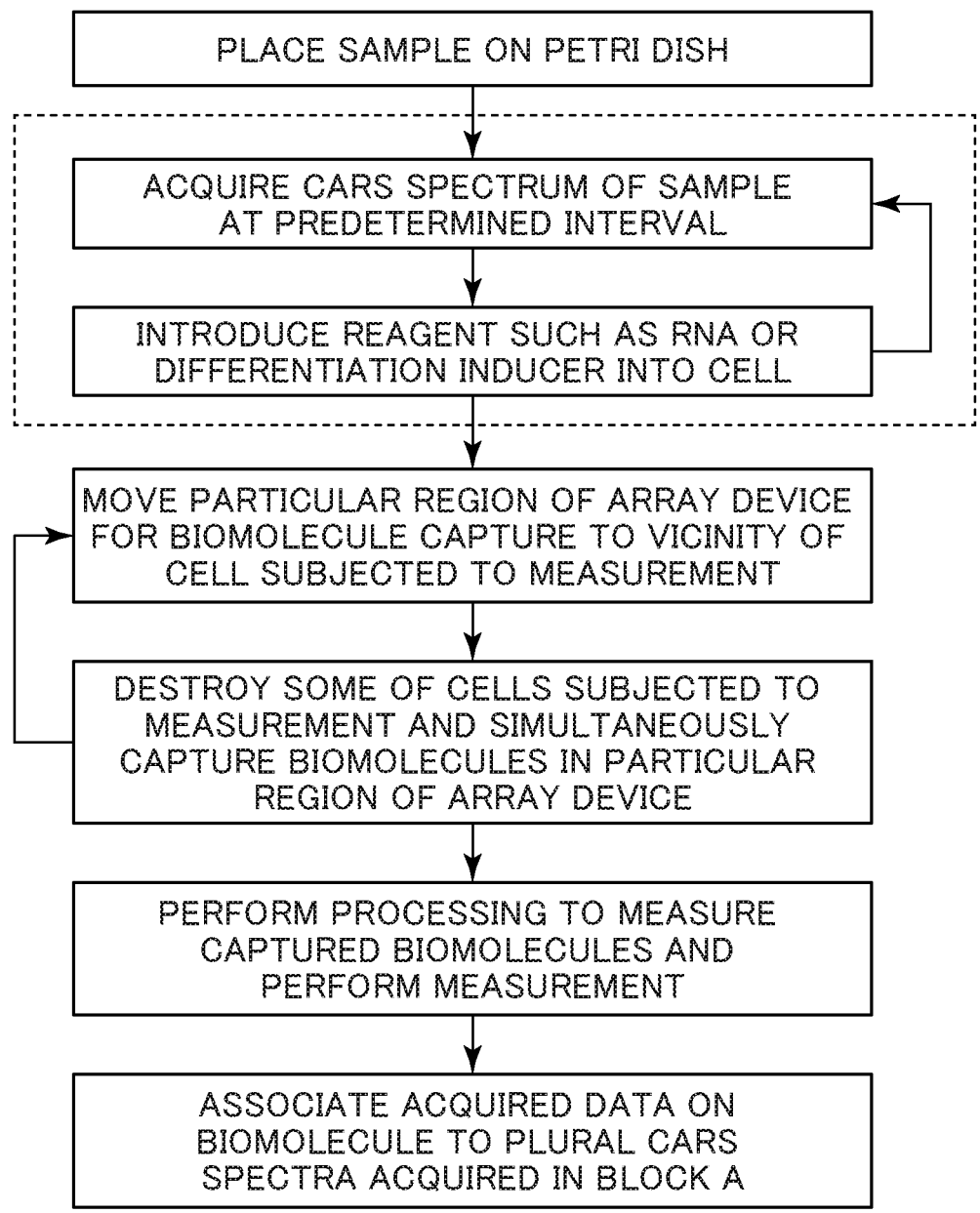
FIG. 13 is a flowchart showing a procedure of gene expression data analysis.

According to the present embodiment, it is possible to acquire the CARS spectrum and the gene expression data with respect to each cell. It is possible to observe the dynamic characteristic of the cell with high accuracy by utilizing this function. FIG. 13 shows a flowchart to perform this analysis.

First, the CARS spectrum is acquired. When it is desired to observe the correspondence between the acquired CARS spectrum and the detailed status of the cell, the cell selected by the user is destroyed, then the biomolecules in the cell are captured on the array device, and the amount of the biomolecules is measured. With the quantitative value of the biomolecules, it is possible to identify the detailed status and type of the cell. With the correspondence with the CARS spectrum, it is possible to associate the CARS spectrum with the cell status and type with high accuracy. Regarding the CARS spectrum, in the point that the Raman spectrum is acquired in comparison with a fluorescence confocal microscope generally used for single cell analysis, it is possible to acquire more information with respect to chemical species of the measurement object, and realize this high-accuracy analysis.

Figure 14:
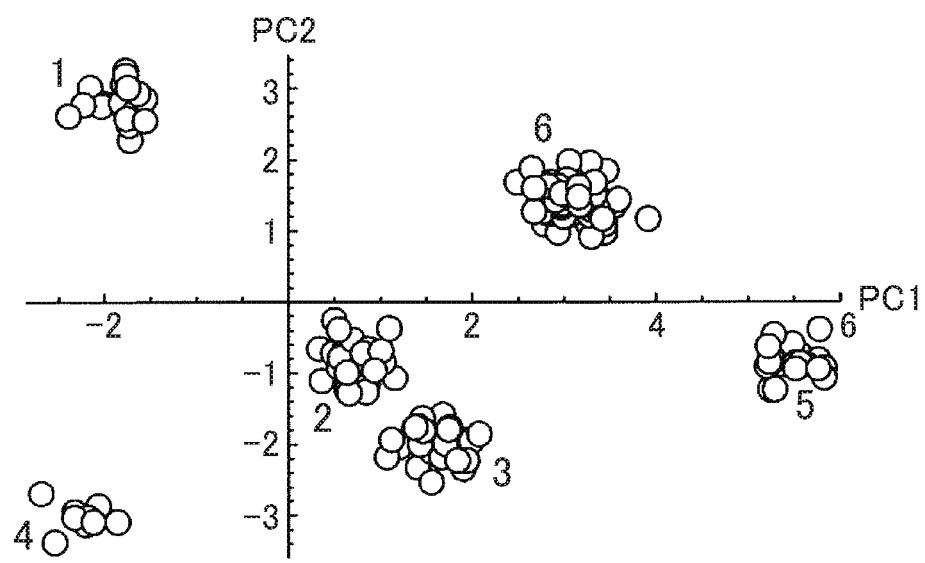
FIG. 14 illustrates a result of main factor analysis.
Figure 15:
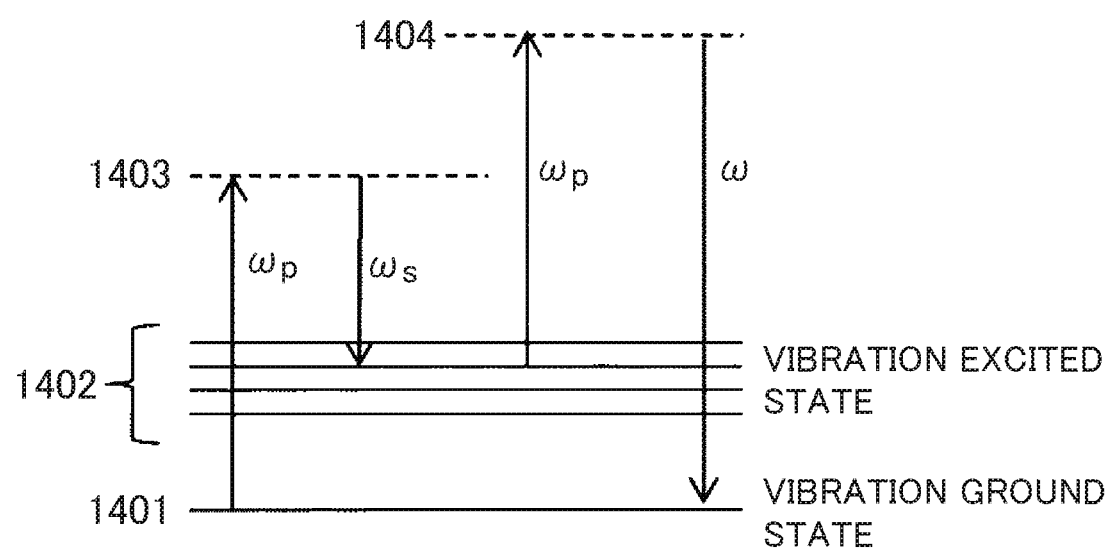
FIG. 15 is an energy diagram showing resonance CARS process.
Figure 16:
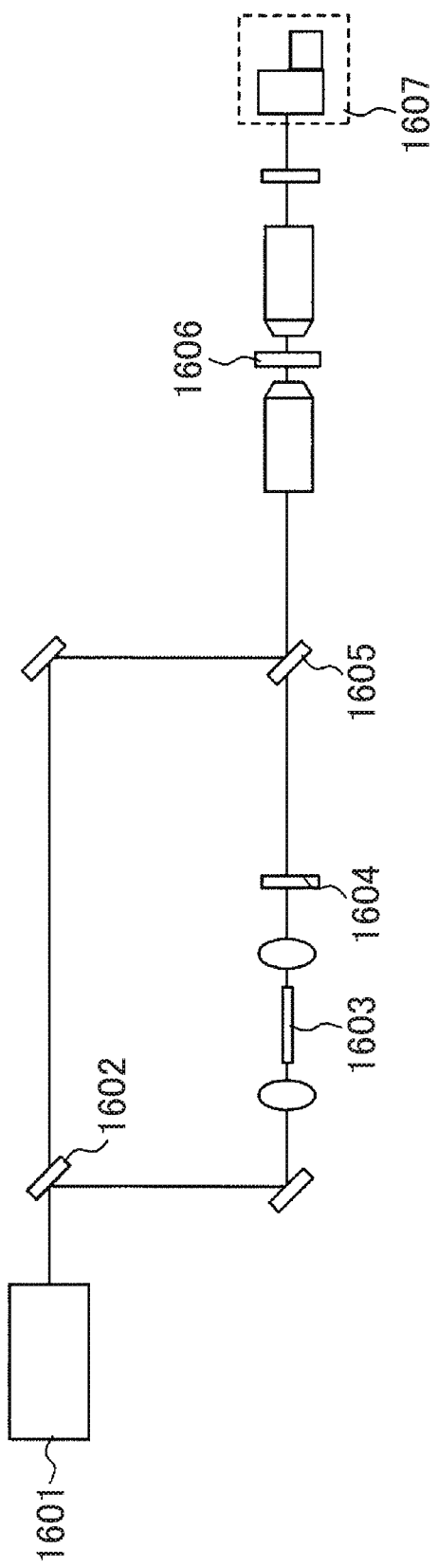
FIG. 16 is a configuration diagram of the conventional multi-color CARS microscope.

Next, a method for cell classification based on CARS spectrum will be shown. FIG. 14 shows, after the acquisition of the CARS spectrum and the quantitative value acquired from the spectrum, a result of plotting of two main factors resulted from gene expression analysis of, e.g., 20 of 180 cells and main factor analysis thereafter. In the figure, PC is abbreviation of "principal component". PC1 denotes a first main factor and PC2 denotes a second main factor. Each point corresponds to gene expression data of one cell. In many cases, the points are divided into plural clusters in correspondence with cell status and type (in this example, six clusters). In FIG. 14, each point corresponds to one cell, and accordingly, even though the type of cell is not determined based on CARS spectrum, it is possible to establish correspondence based on gene expression analysis data. By storing the correspondence in a memory, it is possible to cause a computer system to perform machine learning to determine status or type of a cell based on acquired CARS spectrum and quantitative value. After the completion of the learning, it is possible to classify cell statuses and types only by acquisition of CARS spectrum and quantitative value.

Note that in this example, the main factor analysis is used for the clustering based on cell gene expression. However, various methods such as hierarchical clustering or k-means method are applicable. Further, as a machine learning method, various methods used for data mining such as support vector machine are known, and any of these methods may be used.

Note that the present invention is not limited to the above-described embodiments, but various modifications are included. For example, the above-described embodiments have been described in detail for clearly explaining the present invention, and the invention is not necessarily limited to an embodiment having all the described constituent elements. Further, a part of constituent element of an embodiment may be replaced with a constituent element of another embodiment. Further, constituent elements of an embodiment may be added to those of another embodiment. Further, it is possible to perform addition/deletion/replacement with respect to some of constituent elements of the respective embodiments with other constituent elements.

INDUSTRIAL APPLICABILITY

In accordance with the present invention, it is possible to provide an analysis device which has a simple configuration and which stably operates, and it is possible to accelerate research and development in the field of medical and pharmaceutical industries.

LIST OF REFERENCE SIGNS

2: biomolecule collecting system, 5: cell destruction laser, 11: computer, 21, 22, 23: adhesive systems cultured cell, 30: pore array sheet, 32: platinum electrode, 101: short-pulse laser light source, 103: photonic crystal fiber, 105: long-pass filter, 106: objective lens, 107: sample, 110: spectroscope, 111: spectroscopic unit, 112: detection unit, 201: CCD camera light-receiving unit, 401: illumination, 407: imaging lens, 408: CCD camera, 501: galvanometer mirror

The invention claimed is:

1. An optical analysis device comprising:
   a short-pulse laser light source which emits excitation light in a light beam;
   an optical waveguide that generates super continuum light by photoexcitation based on the excitation light;
   a first collecting optical system comprising an aspherical lens that collects and introduces a light beam from the light source to the optical waveguide;
   a filter that passes all of the excitation light emitted from the optical waveguide and a wavelength component longer than a wavelength of the excitation light, and that eliminates a wavelength component shorter than a wavelength of the light beam from the light source;
   a second collecting optical system comprising an objective lens that collects the light beam passed through the filter to a sample; and
   a spectroscope that detects CARS light generated from the sample.

2. The optical analysis device according to claim 1, wherein the optical waveguide is photonic crystal fiber.

3. The optical analysis device according to claim 2, wherein the length of the photonic crystal fiber is within 1 m.

4. The optical analysis device according to claim 1, further comprising a computer-controlled stage which holds the sample and which controls a relative position between the second collecting optical system and the sample.

5. The optical analysis device according to claim 4, further comprising a mirror that scans an incident angle of the second collecting optical system.

6. A biomolecular analysis device comprising:
   a short-pulse laser light source which emits excitation light in a light beam;
   an optical waveguide that generates super continuum light by photoexcitation based on the excitation light;
   a collecting optical system comprising an aspherical lens that collects and introduces a light beam from the light source to the optical waveguide;

a filter that passes all of the excitation light emitted from the optical waveguide and a wavelength component longer than a wavelength of the excitation light, and that eliminates a wavelength component shorter than a wavelength of the light beam from the light source;

a sample holder that holds a plurality of cells as a sample;

an differential interference microscope that observes the plurality of cells held with the sample holder;

an irradiation optical system comprising an objective lens that collects and irradiates the light beam passed through the filter to the plurality of cells held with the sample holder;

a spectroscope that acquires spectrally coherent anti-Stokes Raman scattering light generated from the plurality of cells by light irradiation;

a detector array that detects the spectrally coherent anti-Stokes Raman scattering light acquired with the spectroscope;

a moveable stage which controls a light irradiation position to the plurality of cells with the irradiation optical system;

a cell destruction laser for destroying the plurality of cells held within the same holder by laser beam irradiation; and a biomolecular capture pore array sheet or semiconductor device that captures a biomolecule in the plurality of cells discharged from the plurality of cells by destruction.

7. The biomolecular analysis device according to claim 6, further comprising a memory for storing the spectrally coherent anti-Stokes Raman scattering light and corresponding data analyzed by using the biomolecular capture pore array sheet or semiconductor device.

* * * * *